(12) United States Patent
Kargar et al.

(10) Patent No.: US 10,278,593 B2
(45) Date of Patent: May 7, 2019

(54) ADAPTIVE CONTROL OF MONITORING DEVICES

(71) Applicants: Soroosh Kargar, Lake in the Hills, IL (US); Steve D. Quam, Carpentersville, IL (US); Hongxuan Zhang, Palatine, IL (US)

(72) Inventors: Soroosh Kargar, Lake in the Hills, IL (US); Steve D. Quam, Carpentersville, IL (US); Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 1037 days.

(21) Appl. No.: 13/923,717

(22) Filed: Jun. 21, 2013

(65) Prior Publication Data

US 2013/0345573 A1 Dec. 26, 2013

Related U.S. Application Data

(60) Provisional application No. 61/662,403, filed on Jun. 21, 2012.

(51) Int. Cl.
*A61B 5/021* (2006.01)
*A61B 5/107* (2006.01)

(52) U.S. Cl.
CPC ............. *A61B 5/021* (2013.01); *A61B 5/107* (2013.01)

(58) Field of Classification Search
None
See application file for complete search history.

(56) References Cited

U.S. PATENT DOCUMENTS

| | | | | |
|---|---|---|---|---|
| 3,541,859 | A | * 11/1970 | Dieter | A61B 5/02152 600/487 |
| 4,669,484 | A | * 6/1987 | Masters | A61B 5/021 33/367 |
| 5,415,431 | A | * 5/1995 | Omura | B60R 22/42 242/374 |
| 6,129,686 | A | 10/2000 | Friedman | |
| 6,171,239 | B1 | * 1/2001 | Humphrey | A61B 5/0482 600/372 |
| 6,245,022 | B1 | * 6/2001 | Archibald | A61B 5/022 600/485 |
| 6,611,783 | B2 | 8/2003 | Kelly, Jr. et al. | |
| 6,661,240 | B1 | 12/2003 | Johnson et al. | |
| 6,753,783 | B2 | 6/2004 | Friedman et al. | |
| 6,791,460 | B2 | 9/2004 | Dixon et al. | |

(Continued)

OTHER PUBLICATIONS

Geng, Z., and M. Jamshidi. "Expert self-learning controller for robot manipulator." Decision and Control, 1988., Proceedings of the 27th IEEE Conference on. IEEE, 1988.*

*Primary Examiner* — Patricia Mallari
*Assistant Examiner* — Jairo H Portillo (57) ABSTRACT

Disclosed herein is a framework for facilitating adaptive control of monitoring devices. In accordance with one aspect, a position detector detects a chest elevation level and provides chest elevation level data. A processor uses the chest elevation level data to determine a heart elevation level with respect to a reference level. A comparator compares the determined heart elevation level with an elevation level of a monitoring device with respect to the reference level. In response to the comparison, a movement system adjusts the elevation level of the monitoring device.

20 Claims, 7 Drawing Sheets

(56) References Cited

U.S. PATENT DOCUMENTS

| | | | |
|---|---|---|---|
| 6,864,795 B2 | 3/2005 | Smith et al. | |
| 6,864,796 B2 | 3/2005 | Lehrman et al. | |
| 6,894,509 B2 | 5/2005 | Johnson et al. | |
| 6,909,374 B2 | 6/2005 | Fong et al. | |
| 7,095,331 B2 | 8/2006 | Lehrman et al. | |
| 7,170,967 B2 | 1/2007 | Dieter et al. | |
| 7,172,340 B2 | 2/2007 | Oota et al. | |
| 7,191,477 B2 | 3/2007 | Hahn et al. | |
| 7,458,685 B2 | 12/2008 | Liang et al. | |
| 7,521,921 B2 | 4/2009 | Zhu et al. | |
| 7,623,622 B2 | 11/2009 | Camus et al. | |
| 7,659,528 B2 | 2/2010 | Uematsu et al. | |
| 7,693,263 B2 | 4/2010 | Bouvier et al. | |
| 7,698,830 B2 | 4/2010 | Townsend et al. | |
| 7,969,316 B2 | 6/2011 | Stumpf et al. | |
| 7,973,626 B2 | 7/2011 | Gerner et al. | |
| 7,986,139 B2 | 7/2011 | Goto et al. | |
| 8,018,224 B2 | 9/2011 | Kurumado et al. | |
| 8,031,132 B2 | 10/2011 | Liou et al. | |
| 8,032,320 B2 | 10/2011 | Sato et al. | |
| 8,052,595 B2 | 11/2011 | Minai | |
| 8,085,153 B2 | 12/2011 | O'Connor et al. | |
| 8,129,933 B2 | 3/2012 | Maeda | |
| 8,140,145 B2 | 3/2012 | Kimura et al. | |
| 8,160,357 B2 * | 4/2012 | Akinyemi | G06T 7/0081 128/922 |
| 8,095,330 B2 | 10/2012 | Kimura et al. | |
| 2003/0093129 A1 * | 5/2003 | Nicolelis | A61B 5/0478 607/45 |
| 2004/0193068 A1 * | 9/2004 | Burton | A61B 5/0476 600/544 |
| 2004/0199081 A1 * | 10/2004 | Freund | A61B 5/022 600/485 |
| 2006/0041281 A1 * | 2/2006 | Von Arx | A61B 5/0215 607/18 |
| 2008/0137806 A1 * | 6/2008 | Chang | A61B 6/032 378/17 |
| 2010/0152600 A1 * | 6/2010 | Droitcour | A61B 5/05 600/534 |

* cited by examiner

| Measurement results Systolic/Diastolic pressure | Monitoring device at fixed position | Monitoring device at adaptive shifting position |
|---|---|---|
| Heart and medical same level | 120/80 | 120/80 |
| Heart system increase 15 cm | 130/85 | 120/80 |
| Heart system increase 15 cm | 117/79 | 120/80 |

| Measured blood pressure values (mmHg) | Heart level difference compared with monitoring device sensors (centimeters) | True patient blood pressure values after adaptive adjustment (mmHg) |
|---|---|---|
| A | ±B | A±c*B |
| 120 | 10 | 121 |
| 130 | -15 | 128.5 |

ADAPTIVE CONTROL OF MONITORING DEVICES

CROSS-REFERENCE TO RELATED APPLICATION

This application claims the benefit of U.S. provisional application No. 61/662,403 filed Jun. 21, 2012, the entire contents of which are incorporated herein by reference.

TECHNICAL FIELD

The present disclosure generally relates to systems and methods for control of monitoring devices.

BACKGROUND

Patient monitoring and patient recording devices are key components in a patient signal and data acquisition system. The acquisition of accurate and stable patient signals, such as invasive blood pressure, non-invasive blood pressure and oximetric patient signals, typically involves a blood pressure transducer, sensors or other patient monitoring devices that are sensitive to their relative level and position (altitude or height) with respect to a patient's heart circulation system.

Patient movement, patient position and altitude level may change during the monitoring process. Such changes may result in unwanted noise and artifacts in patient signals due to relative misalignment between patient heart level and pressure transducers. For instance, variations in the relative position or altitude of an invasive blood pressure (IBP) transducer may lead to errors and inaccuracies in blood pressure measurements that can result in misdiagnosis and delay in treatment. Non-invasive blood pressure (NIBP) measurement requires the position of an arm cuff to be at the same level as the patient's heart. If the blood pressure cuff and patient's heart are at different levels, the acquired NIBP data (e.g., systolic and diastolic pressure values) may show unwanted signal and reading variability that can degrade the accuracy and reliability of signal acquisition and diagnosis.

Known patient monitoring devices are typically installed in a fixed position at the patient's bed side. Different patients may vary in size, position and level (when lying on a patient bed, for example), which may cause different kinds of patient signal measurement variation and errors within such fixed position patient monitoring devices. In addition, such patient monitoring devices are typically not adaptively controlled. When connecting to a patient for a particular medical procedure, a user may need to move the monitoring device even during the medical procedure to ensure high quality signal acquisition and diagnosis. However, such manual adjustment for altitude control is burdensome and difficult, and often unreliable and inaccurate, particularly for high precision control (e.g., in millimeters). Simple patient position checks in a typical operating room (OR) often fails to effectively and comprehensively compensate for patient movement, particularly in the XYZ axes.

As such, there is a need for an improved framework that addresses these deficiencies and related problems.

SUMMARY

The present disclosure relates to a framework for facilitating adaptive control of monitoring devices. In accordance with one aspect, a position detector detects a chest elevation level and provides chest elevation level data. A processor uses the chest elevation level data to determine a heart elevation level with respect to a reference level. A comparator compares the determined heart elevation level with an elevation level of a monitoring device with respect to the reference level. In response to the comparison, a movement system adjusts the elevation level of the monitoring device.

In accordance with another aspect, a position detector detects a chest elevation level and provides chest elevation level data. A processor uses the chest elevation level data to determine a heart elevation level with respect to a reference level. A comparator compares the determined heart elevation level with an elevation level of a monitoring device with respect to the reference level. In response to the comparison, a control unit adjusts signal data provided by the monitoring device and provide compensated signal data for output.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

The present framework advantageously recognizes that the position and/or altitude of the monitoring device relative to the subject are potential sources of inaccuracies in signal acquisition. In some implementations, the present framework automatically and adaptively calibrates the elevation level of the monitoring device so that it is at the same level as the subject's heart. In other implementations, subject signal data is numerically adjusted to provide true measurement values compensated for relative elevation level imbalance. For instance, NIBP-IBP measurement data may be compensated for altitude and/or elevation level differences between a center of a patient's heart system and a patient monitoring (or data acquisition) device. A feedback-loop may be provided to automatically detect elevation level changes and compensate for patient movement.

Figure 1:
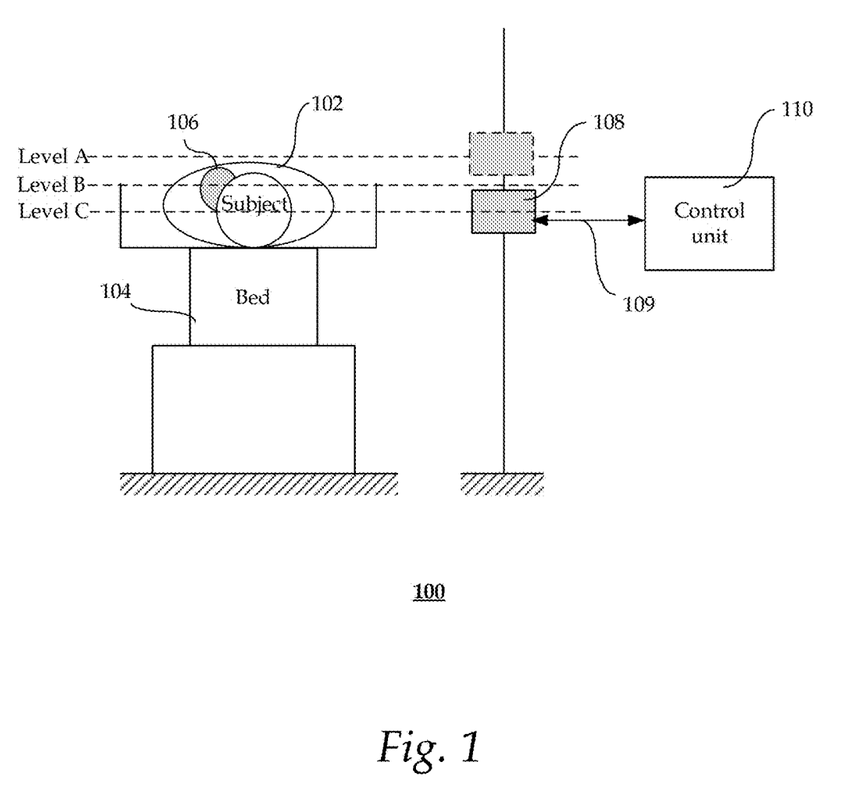
FIG. 1 shows an exemplary configuration during a blood pressure measurement process.

FIG. 1 shows an exemplary configuration 100 during a blood pressure measurement process. As shown, the subject 102 is lying facing upwards on a bed (or patient table) 104, with the subject's heart 106 on the left side of the bed. The monitoring (or recording) device 108 acquires, filters, converts and/or measures signals (e.g., IBP, NIBP, electrocardiogram, intracardiac electrogram, oxygen saturation, Microcap (respiration), temperature, cardiac output, etc.) from the subject 102 via a signal interface to generate subject signal data 109. The control unit 110 uses the signal data 109 from the monitoring device 108 to, for example, generate and display diagnostic data, perform analysis, and so forth.

The monitoring device 108 may be installed at a fixed altitude (or position). For example, the monitoring device may be installed at the bed side and fixed at the rail on the side of the bed 104, such as at elevation level C. As shown, the fixed altitude of the monitoring device 108 may be at different levels relative to the subject's heart 106. For instance, Level A indicates that the center of the monitoring device 108 is higher than the center of the subject's heart 106; Level B indicates that the center of the monitoring device 108 is at the same level as the center of the subject's heart 106; Level C indicates that the center of the monitoring device 108 is lower than the subject's heart 106. The different levels (A, B, C) may be, for example, 10 to 15 centimeters apart.

Figure 2:
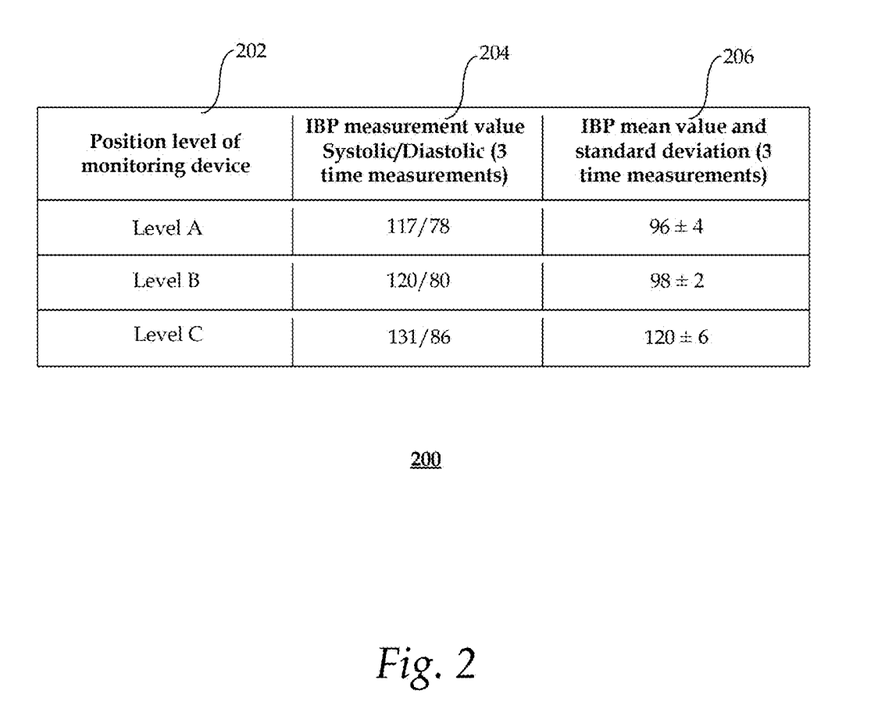
FIG. 2 shows a table containing different IBP measurement values, mean values and standard deviations derived from signals acquired at different elevation levels of the monitoring device.

FIG. 2 shows a table 200 containing different IBP measurement values 204, mean values and standard deviations 206 derived from signals acquired at different elevation levels 202 of the monitoring device 108 (Level A=Level B+10 cm and Level B=Level C+15 cm), as shown in FIG. 1. In table 200, 3-time measurements are acquired for different elevation levels. It can be observed that more data variation and error occurs if the subject's heart 106 and monitoring device 108 are not at the same level (i.e., Levels A and C). In order to obtain more precise and accurate IBP measurements, the present framework may adjust the elevation level or the subject signal data of the monitoring device 108 to compensate for the level imbalance.

Figure 3:
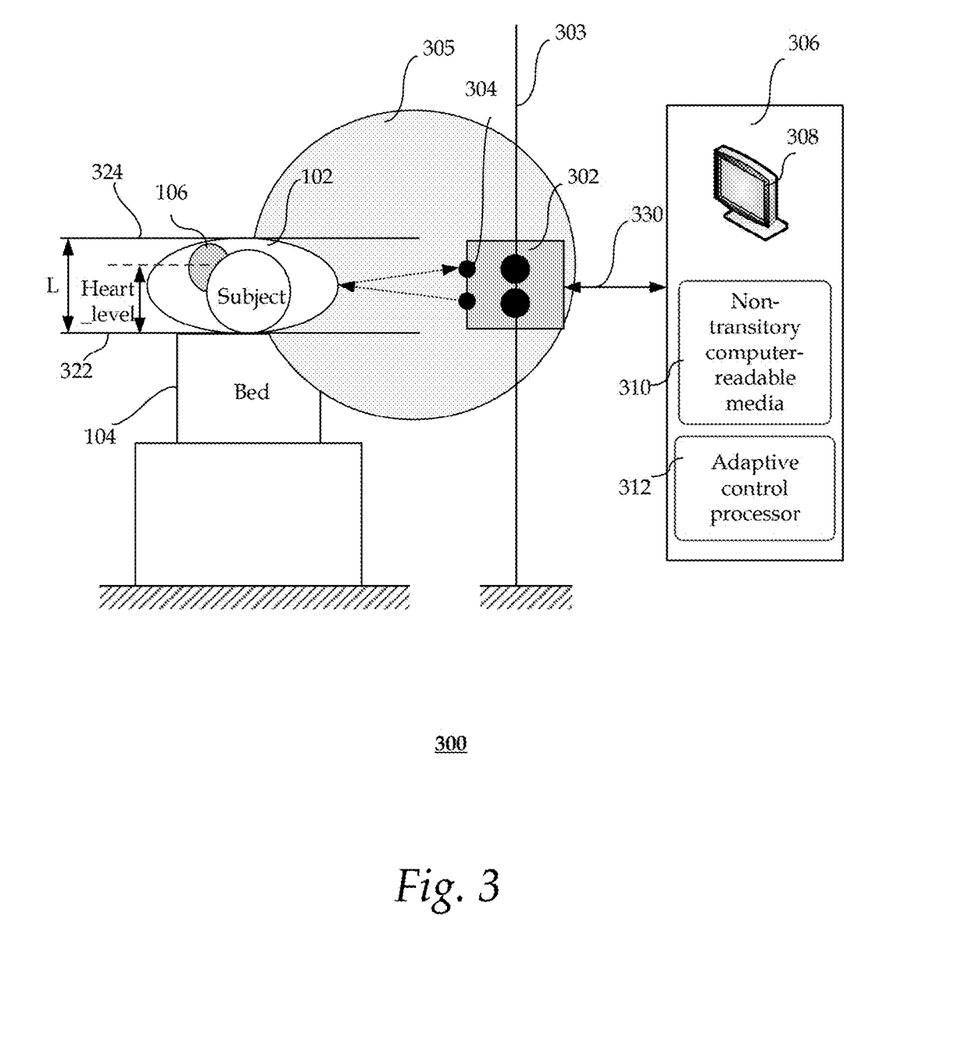
FIG. 3 shows an exemplary monitoring device control system.

FIG. 3 shows an exemplary monitoring device control system 300. The monitoring device control system 300 includes a monitoring device 302 and a control unit 306. The control unit 306 may include, for example, a user interface 308, non-transitory computer-readable media 310 and an adaptive control processor 312. The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 310. Non-transitory computer-readable media 310 may include random access memory (RAM), read only memory (ROM), magnetic floppy disk, flash memory, and other types of memories, or a combination thereof. The computer-readable program code is executed by the adaptive control processor 312 to perform techniques described herein.

The monitoring device 302 may include, for example, a blood pressure monitoring device, such as a blood pressure transducer or sensor, a hemodynamic monitor, an electrophysiological monitor, a vital signs monitor (e.g., Welch Allyn monitor), a Drager patient monitor, and the like. The monitoring device 302 may also be a recording device, such as a signal input box (e.g., Siemens AXIOM Sensis system). Other types of monitoring devices may also be used. The monitoring device 302 may be installed at, for example, a small rail along the side of the bed 104. Depending on the size and weight of the monitoring device 302, it may also be positioned on a mobile trolley or an adjustable vertical arm 303 that can be turned and controlled by a user, as shown in FIG. 3.

The monitoring device 302 may include one or more position detectors 304. The position detectors 304 may be used to detect the altitude or elevation level of the subject 102 or the subject's heart 106, and to provide chest thickness data to the monitoring device 302. The position detectors 304 may be operated in response to a manual command to determine the elevation levels. The shaded area 305 indicates an exemplary effective working area of the position detectors 304. Different methods may be used to detect the altitude or elevation level, such as magnetic impedance, position capacitance, shape and edge detection, image calculation, electromagnetic radiation, etc.

In some implementations, a low energy light (or laser) method is used to detect upper and lower chest elevation levels of the subject 102, which are used to calculate the chest thickness of the subject. For instance, the position detector 304 may include a pair of light emitter and sensor.

The light emitter and the sensor may operate using the same or a controllable wavelength bandwidth. The light emitter and sensor pair 304 detects the lower chest elevation level 322 and the upper chest elevation level 324 for determining the subject's chest thickness (L). Different light (or laser) methods, or other position scanning and detection methods, may be used for detecting the respective elevation levels. In some implementations, an infrared light scanning method is used. Infrared (IR) light is usually visible and directed at a subject's body and bed. Therefore, if a user prefers visible light detection, the infrared spot (e.g., red spot) may be shown on the subject's side or body.

To detect the upper chest elevation level, the height of the light emitter and sensor pair 304 (or the subject 102) may be manually adjusted (e.g., from a reference level to a higher level) until the infrared spot disappears from the subject's body, indicating that the highest elevation level of the subject's chest is reached. Conversely, to detect the lower chest elevation level (or bed top elevation level), the height of the light emitter and sensor pair 304 (or the subject 102) may be manually adjusted from a reference level until the infrared spot disappears from the subject's side, indicating that the lowest elevation level of the subject's chest is reached. The distance L between the upper and lower chest elevation levels may be read from, for example, a movement indicator in the monitoring device 302.

In another implementation, infrared light may be emitted from the light emitter onto the subject's body, and its reflection detected by a light sensor (e.g., photon detector). The light sensor is sensitive to frequency or wavelength of the particular infrared light emitted by the light emitter. The monitoring device 302 may be automatically shifted from a reference level to a higher level using a step motor or any other shifting mechanism. The step motor may be shifted in response to a control signal to accurately determine height changes (e.g., in millimeter range). The monitoring device 302 may be automatically shifted until the upper chest elevation level 324 is detected by the light emitter-sensor pair 304 when there is a significant reduction in the amount of infrared light reflection. Similarly, the lower chest elevation level 322 may be detected by sensing a substantial change in the amount of infrared light reflection. Accordingly, the thickness L of the subject's chest may be automatically derived from the upper and lower chest elevation levels. It should be appreciated that there may be other methods of calculating the subject's chest thickness. For instance, aside from measuring the subject's upper and lower chest elevation levels, other parameters, such as the subject's height or weight, may also be used.

A processor may use the chest thickness data to determine the elevation level of the subject's heart with respect to a reference level. The processor may be implemented in the monitoring device 302 or the adaptive control processor 312. The reference level may be the upper chest elevation level 324 or the lower chest elevation level 322. To determine the distance of the center of the subject's heart to the reference level (hereinafter heart elevation level or "heart_level"), the chest thickness L may be multiplied by a predetermined factor (e.g., a=0.618). For instance, the heart_level may be estimated by the following equation:

$$\text{heart\_level} = a \cdot L = a \cdot |\text{Upper} - \text{Lower}| \quad (1)$$

wherein Upper denotes the upper chest elevation level, and Lower denotes the lower chest elevation level. The predetermined factor a represents the typical ratio of the heart_level to the chest thickness L. In some implementations, the processor selects the predetermined factor a from a plurality of predetermined factors associated with patients having different demographic characteristics. The different demographic characteristics may include age, height, weight, pregnancy status or gender. It may be set at, for example, 0.618 or any other value. The predetermined factor a may be programmed by the user or automatically set by the processor.

The estimated heart_level may then be used to adjust the monitoring device 302 or patient signal data to compensate for relative level imbalance. In some implementations, a comparator is used to compare the estimated heart_level with an elevation level of the monitoring device 302 with respect to a reference level (e.g., upper or lower chest elevation level). The comparator may be implemented in, for example, the control unit 306.

The comparison result may indicate, for instance, that the heart_level is not at the same level as the elevation level of the monitoring device 302. In some implementations, a movement system may be used to adjust the elevation level of the monitoring device 302. For instance, the movement system may adjust the elevation level of the monitoring device 302 to match the estimated heart_level. The center level (e.g., IBP transducer and sensor level) of the patient monitoring device may also be recalibrated. In other implementations, the adaptive control processor 312 may adjust signal data 330 provided by the monitoring device 302 to compensate for the elevation level of the subject's heart in response to the comparison and provide compensated signal data for output.

Figure 4:
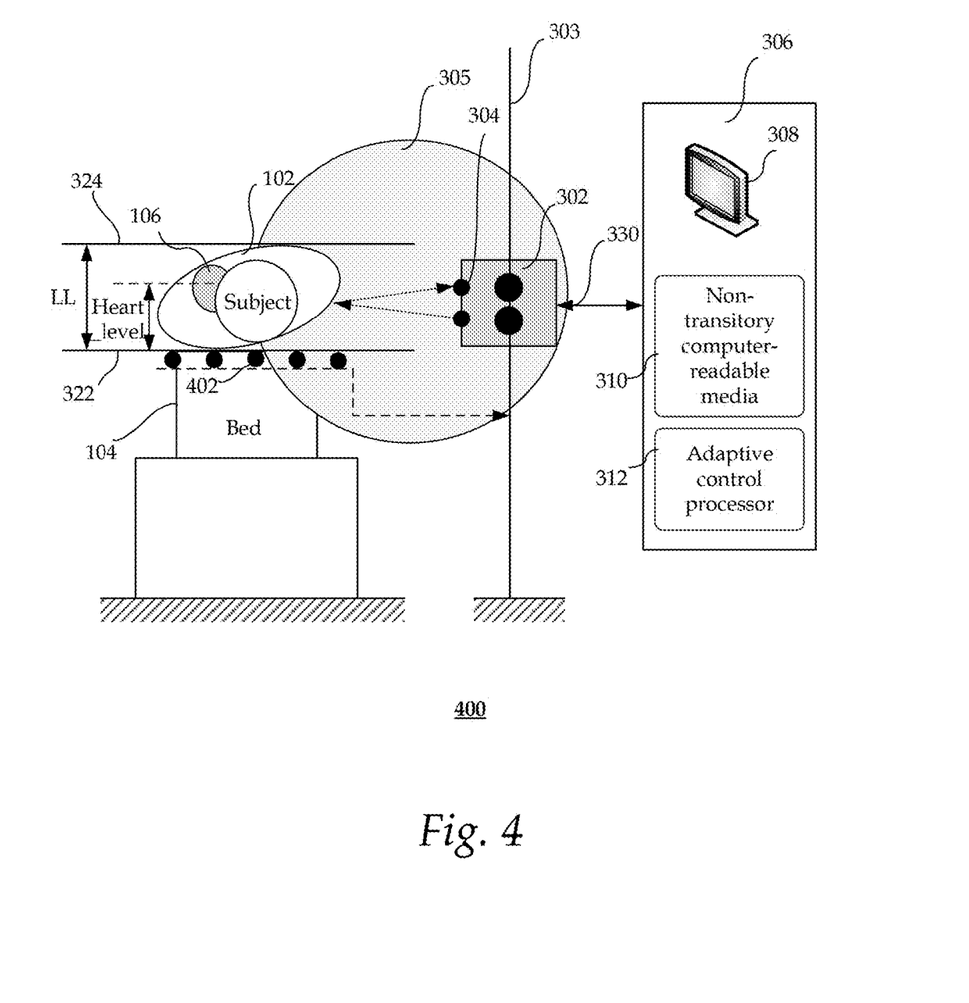
FIG. 4 shows another exemplary monitoring device control system.

FIG. 4 shows another exemplary monitoring device control system 400. Unlike in FIG. 3 where the subject's back is flatly positioned on the bed 103, in this configuration 400, a left movement of the subject's body elevates the right side of the subject's body, thereby causing an increase in the height of the subject's heart (or heart_level). This may occur during a cardiac operation or other clinical procedures. It should be noted that the subject's body may also move on the right side to cause a left side elevation. Since the heart is usually on the left side of the body, left side elevation of the body may result in greater data change compared with right side elevation.

The heart_level may be automatically compensated to take into account such movement. More particularly, the subject's chest thickness may be recalibrated, such as from L to LL. The compensation and recalibration may be implemented automatically and adaptively in accordance with the clinical application and subject's size. For a right-side elevation (as shown in FIG. 4), the height of the subject's heart may be recalibrated as follows:

$$\text{heart\_level}_{right\_elevation} = (a - 0.05) \cdot |\text{Upper} - \text{Lower}| \quad (2)$$
$$= (a - 0.05) \cdot LL$$

For a left-side elevation (not shown), the height of the subject's heart may be recalibrated as follows:

$$\text{heart\_level}_{left\_elevation} = (a + 0.15) \cdot |\text{Upper} - \text{Lower}| \quad (3)$$
$$= (a + 0.15) \cdot LL$$

where LL is the new measured chest thickness, Upper is the upper chest elevation level 324 and Lower is the lower chest elevation level 322. In such implementation, the compensation ratio a for right side and left side elevations are adjusted by predetermined coefficients −0.05 and +0.15 respectively. For different applications and/or patients, these ratios (e.g., a) and coefficients are controlled adaptively and automatically. For instance, they may be determined based on the size of the subject's body, chest size, weight, gender, pregnancy status, etc. Further, they may be preset based on the distance from front to back of the body; the bigger the body size, the bigger the coefficient may be.

Figure 5:
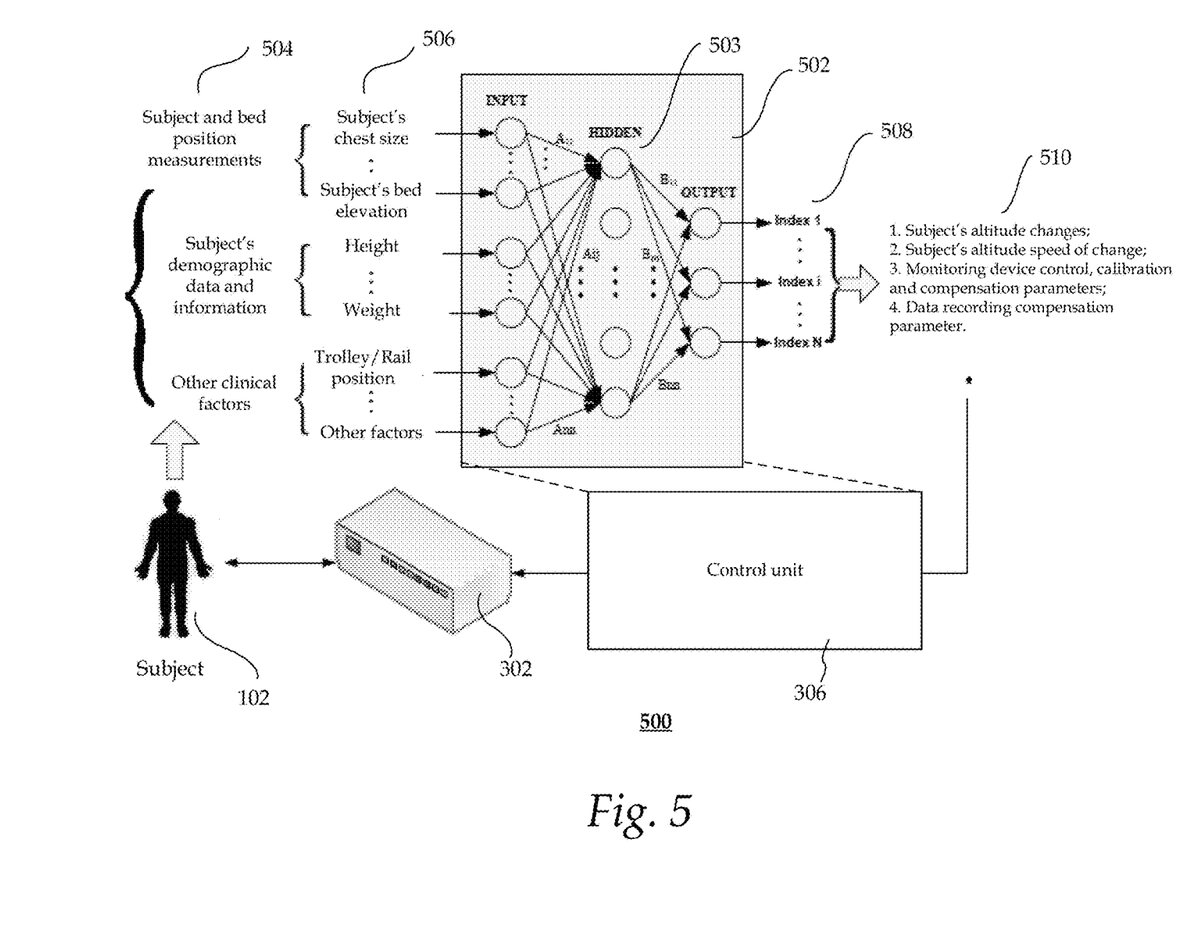
FIG. 5 shows an exemplary artificial neural network (ANN) closed-loop altitude tuning system.

In some implementations, an optional pressure sensor system 402 may be provided to control the position (e.g., trolley or pole position) of the monitoring device 302 in a closed feedback loop. FIG. 5 shows an exemplary artificial neural network (ANN) closed-loop altitude tuning system 500. ANN system 500 includes an ANN unit 502 for altitude and position calibration, calculation and balancing of the monitoring device 302. ANN unit 502 continuously determines the subject's heart elevation level, and provides a closed-loop adaptive control framework for adjusting the monitoring device 302 or signal data in substantial real-time to compensate for level imbalance. ANN unit 502 may be implemented in the control unit 306 or in a separate computing system.

As shown, the ANN structure 503 of the ANN unit 502 may include three layers: input, hidden and output layers. More or less layers may also be provided. Weights $A_{ij}$ are applied between components of the input and hidden layers, while weights $B_{pq}$ are applied between components of the hidden and output layers. The weights ($A_{ij}$ and $B_{pq}$) may be adaptively adjusted and tuned with a training data set. The ANN structure may have a self-learning ability based on new input data 506 which increases the accuracy and precision of the calculated results. Other types of systems, such as fuzzy modeling, expert system or a linear-nonlinear model based controlling and decision system, may also be used.

Using the trained weights, ANN unit 502 integrates and nonlinearly combines multiple kinds of input data or clinical factors (504-506), such as subject and bed position measurements (e.g., subject's chest size, bed elevation, etc.), subject's demographic data and other information (e.g., height, weight, etc.), as well as other clinical factors (e.g., trolley/rail position, etc.). The input data (504-506) is mapped to output parameters 508 that may be used to determine various types of control parameters 510. Such control parameters 510 include, for example, the subject's altitude changes, subject's altitude speed of change, calibration and compensation parameters for controlling or positioning corresponding monitoring device, compensation parameters for data recording, and so forth. Based on these control parameters 510, the control unit 306 may tune or update the altitude or position of the monitoring device 302 by, for instance, controlling the altitude motor coupled to the monitoring device 302.

Figure 6:
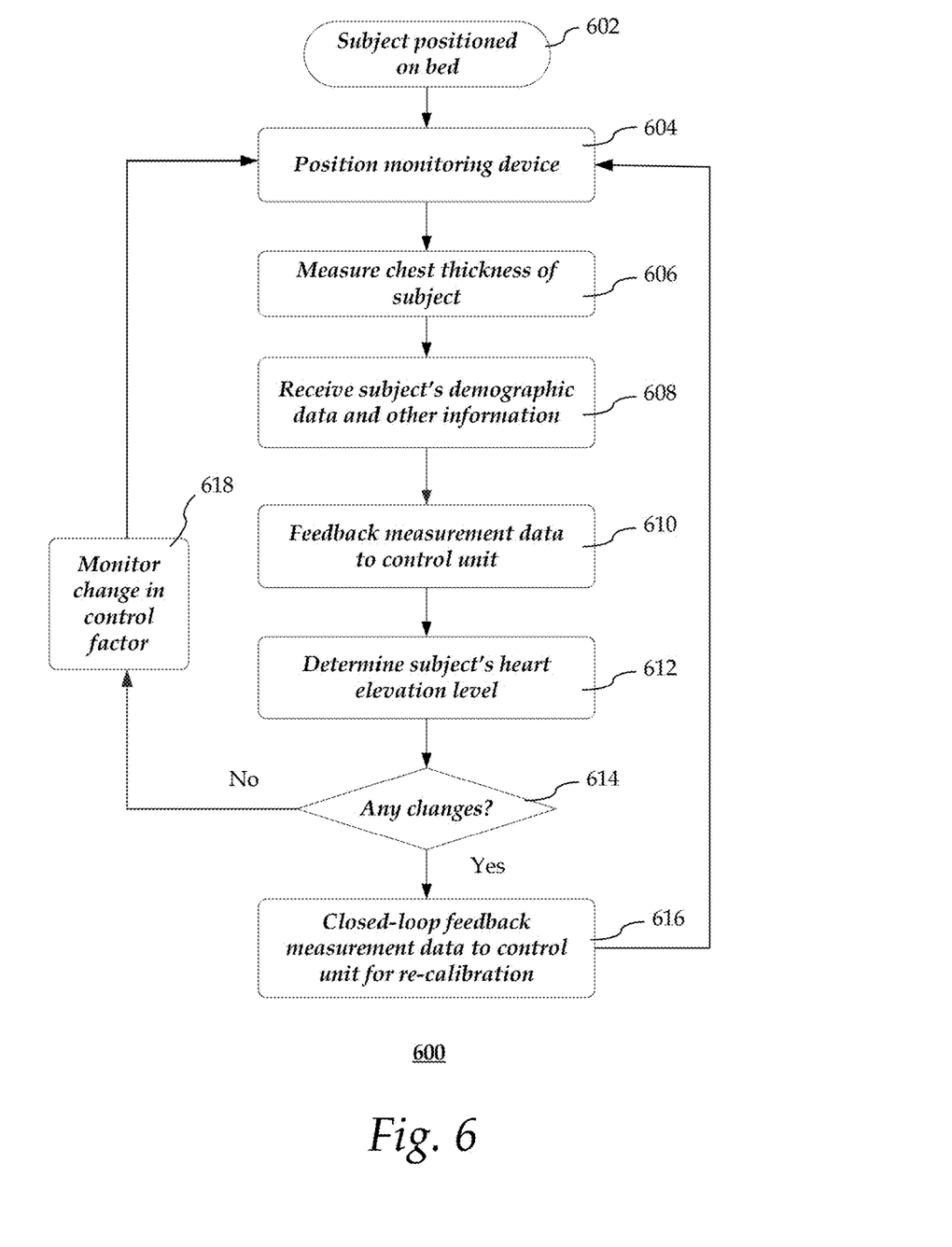
FIG. 6 shows an exemplary method of adaptively controlling a monitoring device.

FIG. 6 shows an exemplary method 600 of adaptively controlling a monitoring device 302. In some implementations, the method 600 monitors and automatically adjusts the elevation level of a monitoring device 302 to the same level as a subject's heart 106, while adaptively matching any movement by the subject 102 or changes in the subject's heart level. The steps of the method 600 may be performed in the order shown or in a different order. Additionally, different, or fewer steps may be provided. Further, the method 600 may be implemented with the system 300 or system 400 of FIGS. 3 and 4 respectively, a different system, or a combination thereof.

At step 602, the subject (or patient) is positioned on a bed or table top. For instance, the subject may be positioned such that the subject is lying flat on the subject's back, as shown in FIG. 3.

At step 604, the monitoring device 302 is positioned at its original position for acquiring signal data. In some implementations, the monitoring device 302 is installed at the side of the bed 104 and on a rail, adjustable arm or mobile trolley 303. Any other methods of installation are also useful. As discussed previously, the monitoring device 302 may include, for example, a blood pressure monitoring device, such as a blood pressure transducer or sensor, or a recording device.

At step 606, the monitoring device 302 measures the chest thickness (L or LL) of the subject's chest. The subject's chest thickness may be estimated by initializing, measuring and/or calibrating the subject's upper and lower chest elevation levels, as discussed previously. The subject's upper and lower chest elevation levels may be measured by, for example, automatically shifting a light emitter-sensor pair 304 until the bed top or chest top is detected.

At step 608, the subject's demographic data and/or other information is provided to the control unit 306. Some or all of such information may be provided via the user interface 308 or retrieved from the non-transitory computer-readable media 310.

At step 610, measurement data from the monitoring device 302 is feedback to the control unit 306. Such measurement data may include, for example, patient movement data, monitoring device movement data, pressure sensor system 402 data, chest thickness (L and LL), and so forth. The measurement data may be provided to the control unit 306 to adaptively control and tune the elevation level of the monitoring device 302.

At 612, the control unit 306 automatically determines the subject's heart elevation level based on the subject's chest thickness (L or LL), as previously discussed. If the monitoring device 302 is at a different elevation level compared to the heart elevation level, the control unit 306 may automatically adjust the elevation level of the monitoring device 302 to the same level as the subject's heart 106.

At 614, the control unit 306 performs real-time monitoring of the measurement data to detect any changes or movement. For example, the control unit 306 may perform a comparison to determine if the subject's heart elevation level relative to the monitoring device 302 has changed. The control unit 306 may automatically perform checks periodically based on preset time steps.

If the control unit 306 detects changes in the measurement data, at 616, the monitoring device 302 provides the new measurement data in a closed-loop feedback to the control unit 306. The new measurement data may be used to re-calibrate and balance the elevation level of the monitoring device 302 such that it is at the same height as the subject's heart elevation level. Such re-calibration tunes the elevation level of the monitoring device 302 to adaptively match any movement and/or heart level changes. The process 600 then returns to step 604 to position the monitoring device 302 at the modified elevation level.

If the control unit 306 does not detect any changes in the measurement data, at 618, the control unit 306 may further monitor for any change in a control factor, such as the time step, controlling speed, etc. Such changes may be initiated by a user via, for example, the user interface 308. Changes in control factors may reset the installation, calibration, etc., if needed. The process 600 then returns to step 604 to install the monitoring device 302 using the modified control factor.

Figure 7A:
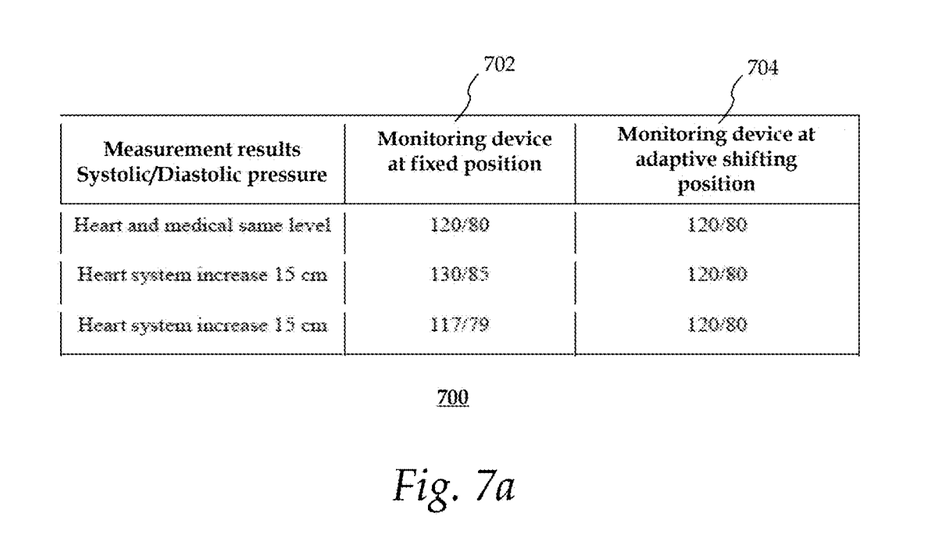
FIG. 7a shows a table illustrating test results for two exemplary scenarios.

In order to validate the method 600, comparison tests were carried out for two scenarios: (1) with a monitoring device (IBP transducer) in a fixed position along the side of the bed; (2) with a monitoring device at a shifting position that is adaptively recalibrated in accordance with the present framework. FIG. 7a shows a table 700 illustrating the test results (702 and 704) for these two exemplary scenarios respectively. Based on the measurement results in the table 700, it can be observed that a monitoring device at a fixed position may not precisely acquire the IBP signal/data due to elevation level and pressure imbalance. It can also be observed that a monitoring device with adaptive and automatic position control based on heart level changes in accordance with the present framework provides improved measurement accuracy and reduced errors and false alarms.

In accordance with one implementation of the present framework, the control unit 306 adjusts the elevation level (height above a reference level) of the monitoring device (or signal acquisition device) 302 in response to a comparison of a determined elevation level of a subject's heart 106 (i.e. heart_level) with an elevation level of the monitoring device 302.

In accordance with another implementation of the present framework, the control unit 306 adjusts signal data (e.g. blood pressure data) in response to the comparison of a determined elevation level of the subject's heart 106 with an elevation level of the monitoring device 302. If the subject's heart level is higher than the monitoring device level, such as a blood pressure transducer and sensor level, the blood pressure measurement is higher than its true value. Similarly, if a subject's heart level is lower than the monitoring device level, the blood pressure measurement is lower than its true value. In view of these observations, the control unit 306 may adaptively perform parameter (coefficient)-based pressure value adjustment based on a correction value retrieved from a repository of information that associates a level difference between a determined elevation level of a subject's heart and an elevation level of a monitoring device with a corresponding correction data value. The control unit 306 may adjust signal data 330 provided by the monitoring device 302 by deriving a correction value from said information repository in response to a level difference determined by the comparison and combining the correction value with a measured value to provide compensated signal data for output.

Figure 7B:
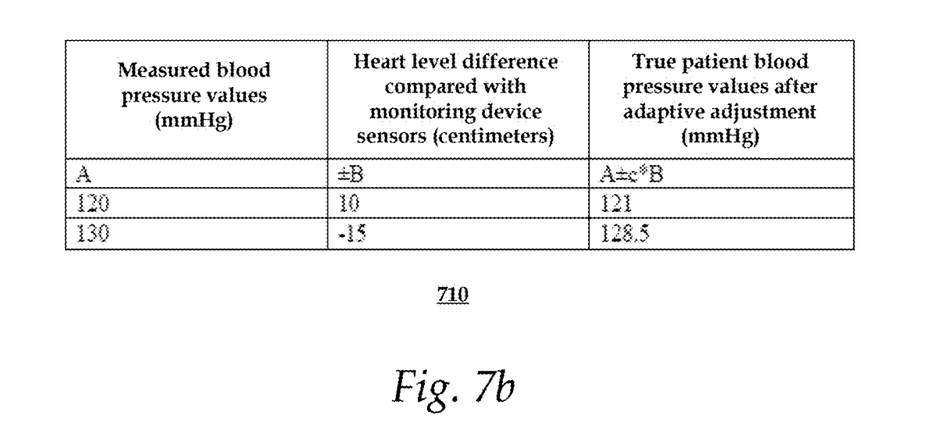
FIG. 7b shows a lookup table that may be used to adjust measured blood pressure values.

FIG. 7b shows a lookup table 710 that may be used to derive a correction value to adjust measured blood pressure values so as to compensate for the imbalance in the subject's heart and monitoring device levels. In the table 710, the correction value c is set at 0.1. If the blood pressure value measured by the monitoring device is A mmHg and the heart level difference is +B cm, the true patient blood pressure is A+0.1*B. The correction value c may be adaptively selected from a plurality of predetermined factors associated with subjects having different demographic characteristics in response to the subject's demographic characteristics (e.g., age, gender, height, weight, pregnancy status, etc.) and clinical conditions (e.g., pathology, medicine, treatment, etc.).

A processor as used herein is a device for executing machine-readable instructions stored on a computer readable medium, for performing tasks and may comprise any one or a combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions that are not performed by a general purpose computer. A processor may be coupled (electrically and/or as comprising executable components) with any other processor enabling interaction and/or communication there-between. Computer program instructions may be loaded onto a computer, including but not limited to a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other devices.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without direct user initiation of the activity. The system and processes of the Figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of the system. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A monitoring device control system, comprising:
a position detector that detects a chest elevation level of a subject and provides chest elevation level data;
a pressure sensor system installed on a bed that provides pressure sensor data associated with the subject;
a processor in a control unit that uses the chest elevation level data to continuously monitor a heart elevation level with respect to a reference level, wherein the control unit recalibrates the heart elevation level in accordance to whether a left movement or a right movement of the subject is detected, wherein recalibration in accordance with left movement differs from recalibration in accordance with right movement for a given subject chest thickness, wherein the control unit further comprises a closed-loop self-learning structure that nonlinearly combines the heart elevation data, the pressure sensor data and a position of a trolley or rail where a monitoring device is installed to generate one or more control parameters; and
a movement system that adjusts an elevation level of the monitoring device in response to the one or more control parameters.

2. The system according to claim 1, wherein the closed-loop self-learning structure comprises an artificial neural network.

3. The system according to claim 1, wherein
the position detector detects chest thickness based on the chest elevation level data and provides chest thickness data, and
the processor uses the chest thickness data to determine the heart elevation level.

4. The system according to claim 3, wherein the processor uses the chest thickness data to determine the heart elevation level by multiplying the chest thickness by a predetermined factor.

5. The system according to claim 4, wherein the processor selects the predetermined factor from a plurality of predetermined factors associated with subjects having different demographic characteristics.

6. The system according to claim 5, wherein the different demographic characteristics comprise age, height, weight, pregnancy status or gender.

7. The system according to claim 4, wherein the processor adjusts the predetermined factor by a predetermined coefficient based at least in part on body size of the subject to compensate for movement of the subject.

8. The system according to claim 1, wherein the movement system adjusts the elevation level of the monitoring device to match the determined heart elevation level.

9. The system according to claim 1, wherein the monitoring device comprises a blood pressure monitor.

10. A system, comprising:
a position detector that includes a light emitter and sensor pair that detects a chest elevation level of a subject and provides chest elevation level data;
a pressure sensor system installed on a bed that provides pressure sensor data associated with the subject;
a processor in a control unit that uses the chest elevation level data to continuously monitor a heart elevation level with respect to a reference level, wherein the control unit recalibrates the heart elevation level in accordance to whether a left movement or a right movement of the subject is detected, wherein recalibration in accordance with left movement differs from recalibration in accordance with right movement for a given subject chest thickness, wherein the control unit further comprises a closed-loop self-learning structure that nonlinearly combines the heart elevation data, the pressure sensor data and a position of a trolley or rail where a monitoring device is installed to generate one or more control parameters; and
a movement system that adjusts an elevation level of the monitoring device in response to the one or more control parameters.

11. The system according to claim 10, wherein the monitoring device comprises a blood pressure monitor.

12. The system according to claim 10, wherein
the position detector detects chest thickness based on the chest elevation level data and provides chest thickness data, and
the processor uses the chest thickness data to determine the heart elevation level.

13. The system according to claim 12, wherein the processor uses the chest thickness data to determine the heart elevation level by multiplying the chest thickness by a predetermined factor.

14. The system according to claim 13, wherein the processor selects the predetermined factor from a plurality of predetermined factors associated with subjects having different demographic characteristics.

15. The system according to claim 10, wherein the closed-loop self-learning structure comprises an artificial neural network.

16. The system according to claim 10, wherein the closed-loop self-learning structure further nonlinearly combines the heart elevation data, the pressure sensor data and the position of the trolley or rail with demographic data.

17. The system according to claim 10, wherein the one or more control parameters comprise altitude change, altitude speed of change, calibration and compensation parameters for controlling or positioning the monitoring device.

18. The system according to claim 10, wherein the light emitter and sensor pair detects upper and lower chest elevation levels.

19. A method of controlling a monitoring device, comprising:
determining a heart elevation level of a subject with respect to a reference level by multiplying a chest thickness of the subject by a predetermined factor, wherein the predetermined factor is adjusted by using a predetermined coefficient based at least in part on body size of the subject and whether a left movement or a right movement of the subject is detected, wherein recalibration in accordance with left movement differs from recalibration in accordance with right movement for a given subject's chest thickness;

determining one or more control parameters by nonlinearly combining, via a closed-loop artificial neural network, the heart elevation level with demographic data of the subject; and adjusting, by a movement system, an elevation level of a monitoring device in response to the one or more control parameters.

20. A method comprising:

determining a heart elevation level of a subject with respect to a reference level by multiplying a chest thickness of the subject by a predetermined factor, wherein the predetermined factor is adjusted by using a predetermined coefficient based at least in part on body size of the subject and whether a left movement or a right movement of the subject is detected, wherein recalibration in accordance with left movement differs from recalibration in accordance with right movement for a given subject's chest thickness;

determining one or more control parameters by nonlinearly combining, via a closed-loop self-learning structure, the heart elevation level with demographic data of the subject and a position of a trolley or rail where a monitoring device is installed; and adjusting an elevation level of the monitoring device in response to the one or more control parameters.

* * * * *